(12) United States Patent
Teugels

(10) Patent No.: US 7,069,788 B2
(45) Date of Patent: Jul. 4, 2006

(54) DOUBLE MEMBRANE TRANSDUCER PROTECTOR

(75) Inventor: Ludwig Teugels, Miramar, FL (US)

(73) Assignee: JMS North America Corp., Hayward, CA (US)

( * ) Notice: Subject to any disclaimer, the term of this patent is extended or adjusted under 35 U.S.C. 154(b) by 118 days.

(21) Appl. No.: 10/745,390

(22) Filed: Dec. 23, 2003

(65) Prior Publication Data

US 2005/0132826 A1 Jun. 23, 2005

(51) Int. Cl.
*G01L 7/00* (2006.01)
(52) U.S. Cl. ........................................ 73/706
(58) Field of Classification Search .................. 73/706;
116/206, 264; 210/321.7, 90, 321.6, 321.69;
600/488; 422/82.05, 82.06
See application file for complete search history.

(56) References Cited

U.S. PATENT DOCUMENTS

| | | | |
|---|---|---|---|
| 3,422,679 A * | 1/1969 | McGowan et al. ............ 73/706 |
| 4,459,139 A * | 7/1984 | vonReis et al. ................... 96/6 |
| 4,493,693 A | 1/1985 | Bilstad et al. |
| 5,215,657 A * | 6/1993 | Goldfield et al. ...... 210/321.64 |
| 5,219,529 A * | 6/1993 | Ngo et al. ................... 422/101 |
| 5,403,279 A * | 4/1995 | Inaba et al. ................... 604/65 |
| 5,603,792 A | 2/1997 | Guala et al. |
| 5,772,624 A | 6/1998 | Utterberg et al. |
| 5,914,033 A * | 6/1999 | Carlsson ...................... 210/90 |
| 6,086,762 A | 7/2000 | Guala |
| 6,168,653 B1 | 1/2001 | Myers |
| 6,346,084 B1 | 2/2002 | Schnell et al. |
| 6,536,278 B1 | 3/2003 | Scagliarini |
| 2004/0237785 A1 | 12/2004 | Neri |

FOREIGN PATENT DOCUMENTS

DE 19816871 10/1999
GB 2168263 6/1986
WO WO 2004/082732 9/2004

* cited by examiner

Primary Examiner—Robert Raevis
(74) Attorney, Agent, or Firm—Morrison & Foerster LLP

(57) ABSTRACT

A transducer protector having at least two filter membranes. In one embodiment, the transducer protector includes a body between two tubular connectors, each of which has a lumen that may be axially aligned. The body lumen is separated from the lumen of each of the tubular connectors by a filter membrane. In one embodiment, the body is transparent and the body lumen has an indicator to alert a user that the filter membrane has been breached by a contaminant so that the user can take immediate steps to prevent further contamination of the system. The configuration of the transducer protector also facilitates the use of separate indicator devices, such as sensor clips.

21 Claims, 3 Drawing Sheets

DOUBLE MEMBRANE TRANSDUCER PROTECTOR

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A COMPACT DISK APPENDIX

Not applicable.

BACKGROUND OF THE INVENTION

Hemodialysis, the most frequently used method for treating advanced and chronic kidney failure consists of a continuous process of removing blood from a patient, cleansing the blood with a special filter mounted on a dialysis machine, and returning the cleansed blood back to the patient. During the hemodialysis procedure, a trained health-care professional will continuously monitor the arterial (pre- and/or post-pump) and venous pressure in the extracorporeal circuit. This is typically done through a tube positioned between the extracorporeal circuit and the dialysis machine. A transducer protector is an in-line sterile barrier and is recommended to be placed between the monitoring line and the dialysis machine. The main purpose of the transducer protector, if correctly used, is to prevent cross-contamination between patients. With dialysis machines, blood must be contained to the extracorporeal circuit, while the safe operation of the dialysis session depends on the ability to accurately measure the pressure in the extracorporeal circuit. The hydrophobic nature of the membrane in the transducer protector prevents fluid (e.g., blood) from passing through the membrane while allowing air to flow freely across the membrane, facilitating accurate pressure measurements. At the end of the dialysis session, the transducer protector and the extracorporeal circuit (blood tubing sets) are discarded and replaced by a new sterile set for the next dialysis sessions.

The transducer protector generally consists of two components sealed around a filtering Hydrophobic membrane, which acts as a sterile barrier. The two components can be any combination of a male-male, female-female and male-female connectors that attach to medical equipment. The transducer protector is essential in shielding the dialysis equipment and patients from risks of contamination by infected blood. Typical transducer protector devices are described in U.S. Pat. Nos. 5,500,003 and 5,603,792 to Guala et al.; U.S. Pat. No. 6,086,762 to Guala; U.S. Pat. No. 6,168,653 to Myers and U.S. Pat. No. 6,536,278 to Scagliarini. These references all disclose transducer protectors of various configurations, but with the common features described above of a single filtering membrane between two tubular connectors.

Due to the high risk of blood contamination and incidents involving wetted/breached membranes in transducer protectors, which can occur due to fluctuation of fluid levels in the arterial and/or venous drip chamber, as well as due to changes of pressures in the extracorporeal circuit, it has become necessary to provide further protection between the pressure-sensing port of the hemodialysis machine and the extracorporeal circuit. Proposals for further protection include placing one or more redundant transducer protectors in the system and/or utilizing transducer protectors with luer extensions so that visual inspection of failure is facilitated. However, drawbacks to these solutions include, but are not limited to, the fact that they are bulky to use, they offer increased risk of non-sterile procedures, and they generally employ poor connections between the different transducer protectors.

Therefore, it would be desirable to provide a transducer protector that would provide increased protection, would reduce necessary handling and connecting, would maintain connection sterility, would increase more precise pressure monitoring, and would reduce inventory control, thus providing cost savings to the users.

BRIEF SUMMARY OF THE INVENTION

Accordingly, the present invention comprises a transducer protector device, comprising a first tubular connector being configured for connection to a monitoring tube which is connected to the extracorporeal circuit, a second tubular connector being configured for connection to a nipple (pressure sensing port) of the dialysis machine, and a body positioned between said first and second tubular connectors, wherein a first filter member is positioned between said body and said first tubular connector, and wherein a second filter member is positioned between said body and said second tubular connector.

The body and first and second tubular connectors can include axially aligned lumen and can be connected together via ultrasonic welding, heat sealing, RF welding and even self-adhesive patches. In one embodiment of the invention, the first and second tubular connectors have a luer connector end and a flanged end, the flanged end for the first and second tubular connectors each being configured for mating with flanged ends on the body. The first tubular connector may have a male luer connector and the second tubular connector may have a female luer connector. However, such connector types can be reversed or both connectors can be either a male connector or a female connector. Further, the connectors can be fashioned as neither male or female, but instead in the configuration of a slip end. Moreover, the first and second filter members can be secured in place between the mating portion of the flanged sections of the body and the first and second tubular connectors. In addition, an indicator may be provided between the first and second filter members either in a lumen of the body or in an area where the body and the tubular connectors meet. The indicator can be in the form of a biological or chemical material and may include the feature of changing color upon contact with a bodily fluid. The indicator can also be in the form of a sensor, which may be attached via mechanical means to the transducer protector.

These and other embodiments, features and advantages of the present invention will become more apparent to those skilled in the art when taken with reference to the following more detailed description of the invention in conjunction with the accompanying drawings that are first briefly described.

DETAILED DESCRIPTION OF THE INVENTION

The following detailed description should be read with reference to the drawings, in which like elements in different drawings are identically numbered. The drawings, which are not necessarily to scale, depict selected preferred embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

The present invention is directed to a transducer protector containing more than one filter membrane so that detection of a breached or wetted membrane can lead to prevention of system contamination (in contradistinction to the prior art devices in which detection of a breached or wetted membrane could likely lead to extensive system contamination). To that end, the examples herein are directed to a transducer protector having two filter membranes that are spaced apart by a body having a length. It should be appreciated, however, that although the examples and embodiments described herein are in connection with a transducer protector having two filter membranes, it is equally within the scope of the present invention for the transducer protector to contain a number of filter membranes, i.e., three, four, five, etc., the thrust of the invention being that multiple barriers within a single device are provided. Additionally, the present invention is directed to a transducer protector that contains within it a biological and/or chemical indicator to alert a clinician or physician that a potential contaminant has bypassed the initial barrier (membrane).

By providing a single transducer protector that includes more than one filter membrane along with an optional detection system, various objectives are achieved. Notably, utilization of such a transducer protector in a system would be advantageous over systems having two or more independent transducer protectors in that there is a reduction in the necessity of handling and connecting and hence a reduction for a possible contamination risk caused by a non-sterile technique when connecting two or more transducer protectors, and the inventory control is reduced by at least half. Moreover, incorporating multiple filters into one device ostensibly provides cost savings to the users. Additionally, the use of one, as opposed to multiple, separate transducer protectors provides increased sterility and should enable more precise pressure monitoring.

Figure 1:
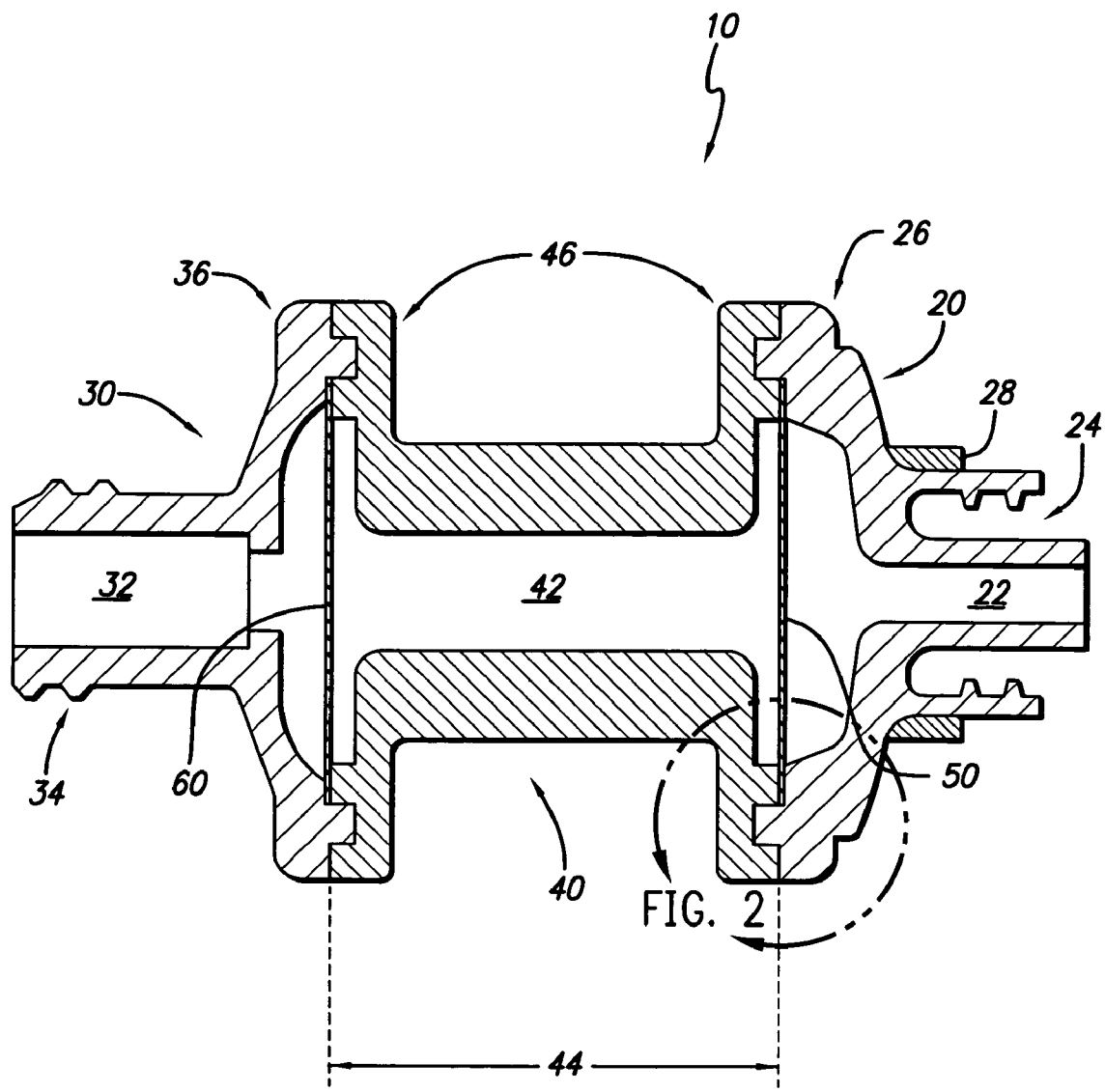
FIG. 1 is a transducer protector according to the present invention, shown in cross-section.
Figure 2:
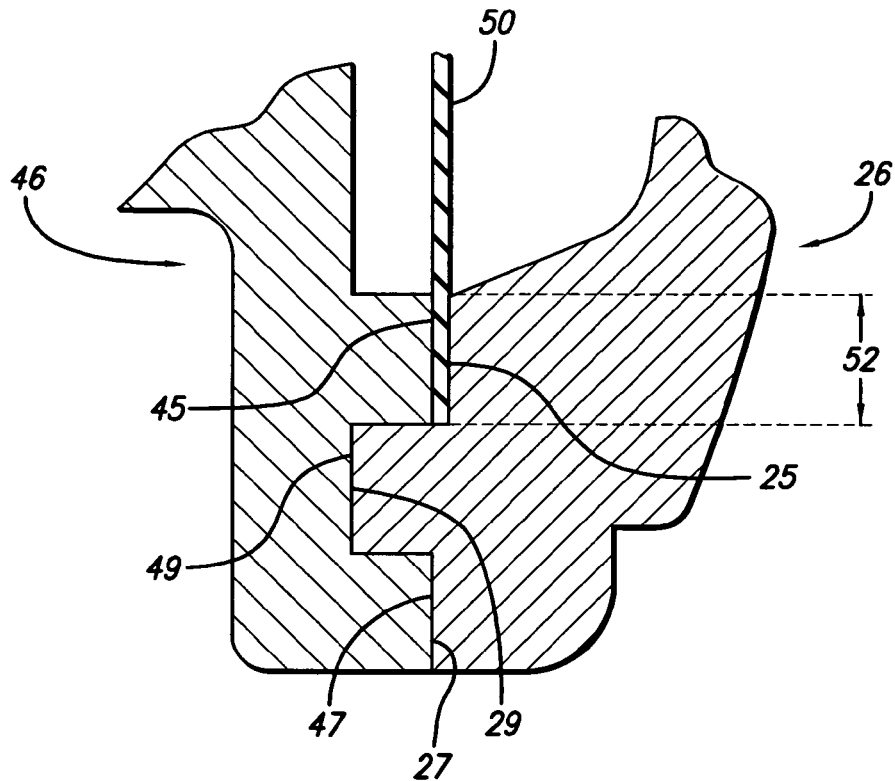
FIG. 2 is an enlarged view of section "2" indicated in FIG. 1.

Referring now to FIG. 1, a transducer protector 10 of the present invention is illustrated, having a first tubular connector 20, a second tubular connector 30 and a body 40. The first tubular connector 20 has a lumen 22 and a female luer connector 24. The first tubular connector 20 is attached to the body 40 along a flanged section 26, while the second tubular connector 30 is attached to the body 40 along a flanged section 36. The body 40 has flanged areas 46 that are configured to mate with flanged sections 26, 36. More particularly, as seen in FIG. 2 in connection with the first tubular connector 20 and the body 40, flanged section 26 contains receiving portions 25, 27 and a projection 29, which correspondingly mate with projections 45, 47 and receiving portion 49. In this embodiment, ultrasonic welding connections between the flanged sections 26 and 46 occur circumferentially along the aforementioned mating portions and projections to seal the body 40 to the first tubular connector 20. The second tubular connector 30 is likewise attached to the body 40. Of course, it should be appreciated that the body 40 could be connected to the tubular connectors 20, 30 by many other methods other than ultrasonic welding, including, but not limited to, use of adhesives, heat sealing, RF welding, and even self-adhesive patches.

As shown in FIGS. 1 and 2, between both tubular connectors 20, 30 and the body 40, there is positioned filter membranes 50, 60 respectively. Filter membranes 50, 60 can be made of PTFE (polytetrafluoroethylene), although certainly other materials such as polypropylene, PES, PVDF (polyvinylidene difluoride), acrylic copolymer and other combinations of polymeric materials, would also be suitable for forming a contaminant barrier. The filter membranes 50, 60 are attached in place at the periphery thereof, being sandwiched between the body 40 and the tubular connectors 20, 30, respectively. With reference to tubular connector 20 and body 40, the sandwiching of the filter membrane 50 occurs between receiving portion 25 and projection 45, as shown in FIG. 2. In order to ensure that filter membrane 50 is secured in place, a length 52 must be between the respective body portion and tubular connector portion (in this case, receiving portion 25 and projection 45). Of course, depending on the materials involved and method of attachment, this required length can vary. In this embodiment, length 52 is between the range of approximately 2 mm to 10 mm. It should be appreciated that filter membrane 60 is similarly secured in place along a necessary length between flanges 36 and 46.

Referring again to FIG. 1, the first tubular portion 20 is shown with a female luer connector 24, which in this embodiment is configured for connection with a male luer connector (not shown) on the sterile side of the transducer protector 10, or the side connected to the dialysis machine. The second tubular portion 30, on the other hand, is shown with a male luer connector, which in this embodiment is configured for connection with a female luer connector (not shown) on the non-sterile side of the transducer protector 10, or the side connected to a gauge or other pressure sensitive device. Of course, the connectors on either the sterile or non-sterile side can be of many different types, depending on the connection requirements of the system. First tubular connector 20 has a lumen 22, which, when connected, is in fluid communication with tubing (not shown) connected to a dialysis machine, whereas second tubular connector 30 has a lumen 32, which, when connected, is in fluid communication with tubing (not shown) connected to a pressure sensitive device.

Body 40 has a lumen 42, which in this embodiment is axially aligned with the lumens 22, 32 of the tubular connectors 20, 30 respectively. In the preferred embodiment, the body 40 is made of a transparent material so that the lumen 42 can be seen by the clinician or physician that is monitoring the transducer protector 10. Thus, if blood comes through lumen 22 and into contact with the filter membrane 50 and contaminant enters lumen 42, the clinician or physician will be able to take immediate action to prevent further progress of the blood or contaminant toward and in contact with the filter membrane 60. To further this goal of providing time to prevent contamination, the filter membranes 50 and 60 should be separated by a distance, which distance in this embodiment would be length 44. In the described embodiment, the optimal distance between the filter membranes 50,60 to provide adequate warning, while maintaining an acceptable size has been found to be in the range of approximately 15 mm to 30 mm. However, depending on the materials of the parts and/or the particular application, certainly this distance could be shortened or extended and any distance would be within the scope of the present invention.

Figure 3:
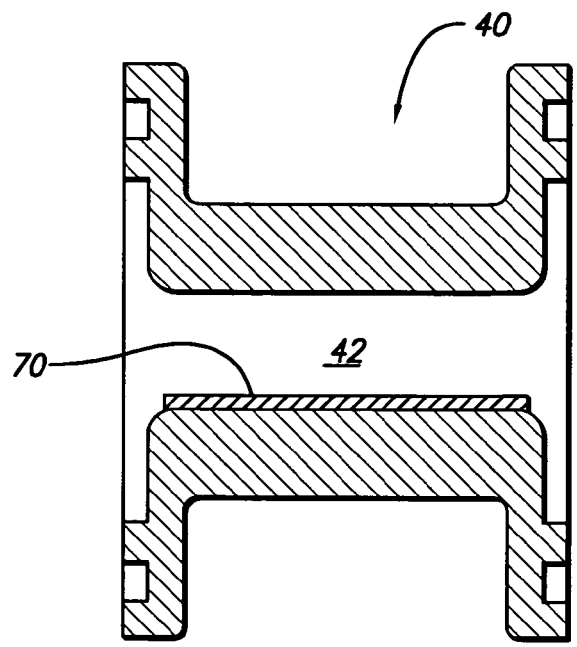
FIG. 3 is a view, in isolation, of the body of the transducer protector of FIG. 1, illustrating an alternate embodiment of the present invention.

Referring to FIG. 3, furthering the goal of providing a means of detection for a clinician or physician monitoring a dialysis system, an embodiment is shown in which the body lumen 42 has a coating 70 thereon to assist in providing a signal to the clinician or physician regarding fluid or airborne pathogens that have progressed beyond the filter membrane 50. The coating could, for example, immediately change color upon contact with a contaminant, such as blood, to provide the signal to the clinician. Of course, many different materials would be possible for the coating 70, as would be apparent to one of skill in the art, which could provide a number of different indicators other than a color change. While the coating is shown on a certain section of a wall of the lumen 42, certainly as necessary, the entire circumference of the wall could be coated. Likewise, although a majority of the length of the lumen 42 is shown with a coating 70 thereon, it should be appreciated that smaller or longer segments of the lumen 42 could be coated, depending on the particular materials used and/or the application involved. Moreover, while a coating 70 is shown, various different chemical or biological indicators are also possible in place of or in addition to the coating 70, as would be apparent to one of skill in the art.

Figure 4:
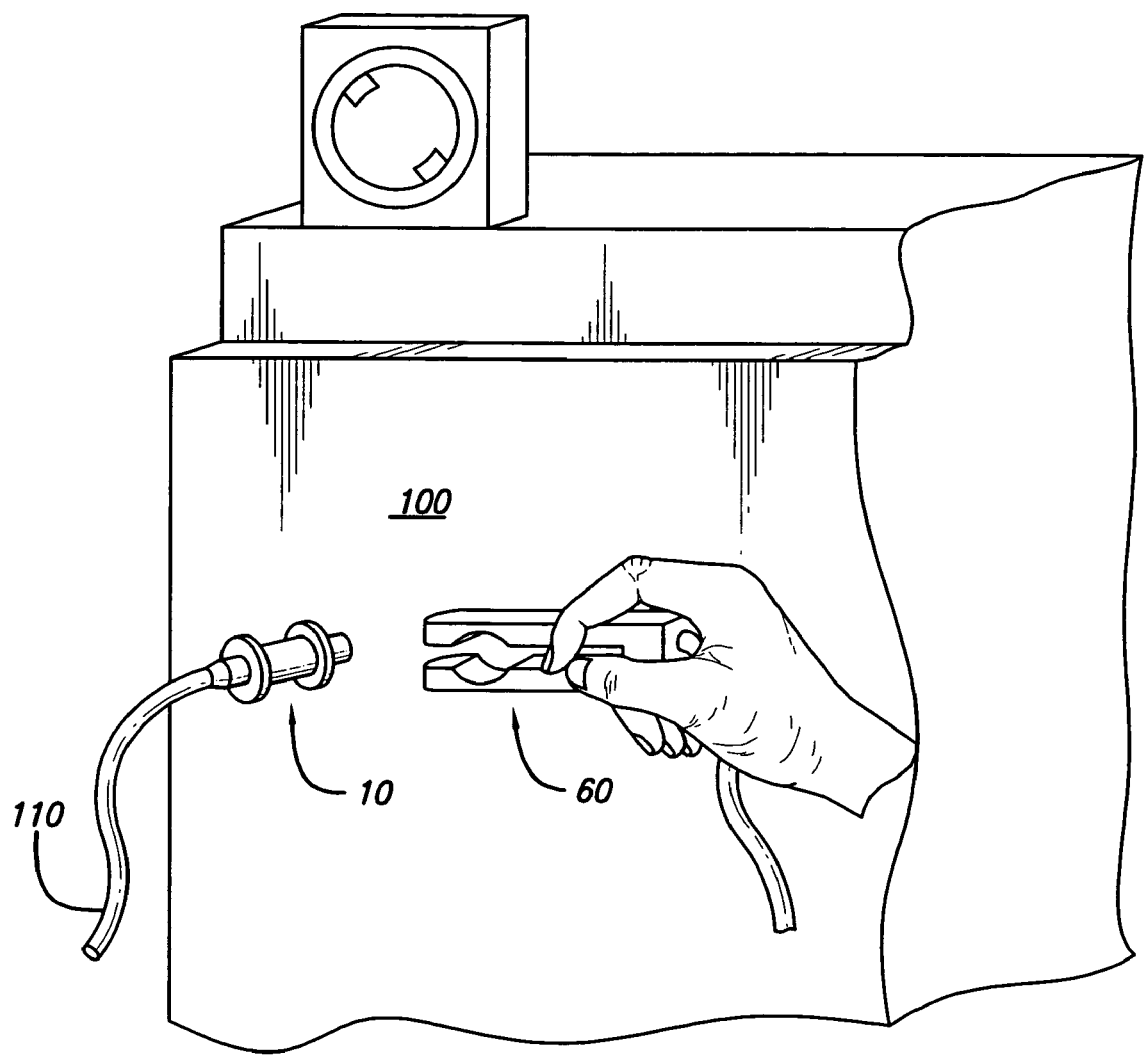
FIG. 4 is a perspective view of the transducer protector of FIG. 1 attached to a dialysis machine, illustrating the use of a sensor clip therewith.

FIG. 4 illustrates a further means of monitoring the transducer protector 10. In this embodiment, the transducer protector 10 is attached to a dialysis machine 100 on one side and to a monitoring line 110 of a blood tubing set on the opposite side. A sensor clip 60 is then clipped to the body 40. The sensor clip 60 utilizes optical or other means to detect whether a contaminant is present in the body lumen 42 after having breached the filter membrane separating the monitoring line 110 from the body 40. Once a contaminant is detected, a signal is immediately transmitted to a warning device, which can be incorporated into a dialysis machine or can be a stand alone device, which alerts the clinician that a breach has occurred. Due to the dual membrane properties of the transducer protector 10, the clinician is able to prevent the contaminant from reaching the dialysis machine 100. It should be understood that the sensor clip 60 could be used in combination with or instead of any of the aforementioned means of detection.

The present invention has been described above in terms of certain preferred embodiments so that an understanding of the present invention can be conveyed. However, there are many alternative arrangements not specifically described herein but with which the present invention is applicable. Although specific features have been provided, the device of the present invention would equally be embodied by other configurations not specifically recited herein. The scope of the present invention should therefore not be limited by the embodiments illustrated, but rather it should be understood that the present invention has wide applicability with respect to transducer protectors generally. All modifications, variations, or equivalent elements and implementations that are within the scope of the appended claims should therefore be considered within the scope of the invention.

What is claimed as new and desired to be protected by Letters Patent of the United States is:

1. A transducer protector device, comprising:
   a first connector configured for connection to a first tube;
   a second connector configured for connection to a second tube;
   a body including a lumen positioned between said first and second connectors, a first filter member having a portion captured between a first surface of said body and said first connector, and a second filter member having a portion captured between a second surface of said body and said second connector; and
   an indicator disposed in the body.

2. The device according to claim 1, wherein said body and said first and second connectors are hermetically sealed together.

3. The device according to claim 1, wherein said body is ultrasonically welded to said first and second connectors.

4. The device according to claim 1, wherein the distance between said first and second filter members is in the range of approximately 1 mm to 20 mm.

5. The device according to claim 1, wherein said first connector comprises a female connecting member and said second connector comprises a male connecting member.

6. The device according to claim 1, wherein the body lumen is in axial alignment with a lumen of the first connector and a lumen of the second connector.

7. The device according to claim 1, wherein said body is made of a transparent material.

8. The device according to claim 7, wherein the indicator comprises a biological or chemical indicator.

9. The device according to claim 1, wherein the indicator comprises a biological or chemical indicator.

10. The device according to claim 9, wherein said biological or chemical indicator comprises a coating on an inner surface of said lumen.

11. The device according to claim 9, wherein said biological or chemical indicator comprises a material that changes color upon contact with bodily fluid.

12. The device according to claim 1, wherein at least one of the first and second filter members are comprised of a material selected from the group consisting of PTFE, PES, PVDF, acrylic copolymer, or polypropylene and combinations thereof.

13. A transducer protector device, comprising:
   a first tubular connector having a first and a second end and a lumen therebetween, said first end comprising a female connector luer, said second end comprising a flange;
   a second tubular connector having a first and a second end and a lumen therebetween, said first end comprising a male connector luer, said second end comprising a flange;
   a body positioned between said first and second tubular connectors, said body having a first and a second end and a lumen therebetween, said first and second ends comprising first and second flanges respectively;
   a first filter member captured between said first tubular connector flange and said first body flange;
   a second filter member captured between said second tubular connector flange and said second body flange; and
   an indicator disposed in the body.

14. The device according to claim 13, wherein said body and said first and second tubular connectors are hermetically sealed together.

15. The device according to claim 13, wherein said first and second body flanges are ultrasonically welded to said first and second tubular connector flanges respectively.

16. The device according to claim 13, wherein said body comprises a transparent material.

17. The device according to claim 16, wherein the indicator comprises a biological or chemical indicator.

18. The device according to claim 17, wherein said biological or chemical indicator comprises a coating on an inner surface of said lumen.

19. The device according to claim 17, wherein said biological or chemical indicator comprises a material that changes color upon contact with bodily fluid.

20. The device according to claim 17, further comprising a sensor clip attached to said body, wherein said sensor clip utilizes optical means to detect the presence of a contaminant within said body lumen.

21. The device according to claim 13, wherein at least one of the first and second filter members are comprised of a material selected from the group consisting of PTFE, PES, PVDF, acrylic copolymer, or polypropylene and combinations thereof.

* * * * *